United States Patent [19]

Taldo et al.

[11] 4,402,331

[45] Sep. 6, 1983

[54] PORTABLE LAVAGE DEVICE

[75] Inventors: Terry J. Taldo, Grand Prairie; Kenneth R. Jackson, Arlington, both of Tex.

[73] Assignee: Delta Manufacturing and Sales, Inc., Tex.

[21] Appl. No.: 248,510

[22] Filed: Mar. 27, 1981

[51] Int. Cl.³ .............................................. B08B 3/02
[52] U.S. Cl. .................................... 134/58 R; 134/98; 134/178; 134/194; 134/199; 137/624.13; 128/66; 239/447
[58] Field of Search ................... 134/34, 58 R, 96–98, 134/173, 175, 177–178, 191, 194, 199–200; 137/624.13; 138/46; 239/447; 128/66

[56] References Cited

U.S. PATENT DOCUMENTS

| | | |
|---|---|---|
| 3,227,158 | 1/1966 | Mattingly ............................... 128/66 |
| 3,416,544 | 12/1968 | Paiva .................................. 134/200 X |
| 3,699,984 | 10/1972 | Davis ................................. 134/199 X |
| 3,757,806 | 9/1973 | Bhaskar et al. ..................... 134/191 |
| 3,918,987 | 11/1975 | Kopfer ............................... 134/199 X |

Primary Examiner—Robert L. Bleutge
Attorney, Agent, or Firm—Sigalos & Levine

[57] ABSTRACT

A portable lavage device comprising a moveable tank for holding a cleansing liquid, a pump coupled to the tank for circulating the cleansing liquid under a pressure which varies from a maximum to a minimum and spaced nozzles coupled to the circulating pump and arranged to spray the cleansing liquid under varying pressure against an item to be cleaned.

21 Claims, 16 Drawing Figures

PORTABLE LAVAGE DEVICE

BACKGROUND OF THE INVENTION

The present invention relates to a cleansing device and in particular to a device for surgically scrubbing and cleansing the hands and arms of a surgeon.

It is well known that, under emergency conditions, the survival of a patient often depends on the time elapsing while the surgical teams scrubs before entering the operating room. The typical pre-surgical scrub requires a time duration of five to fifteen minutes according to the type and length of the planned operation. In the past, the pre-surgical scrubbing of the surgeons and operating room personnel has followed the same pattern. Scrub brushes and various chemicals are used in order to free the hands from the bacteria which may contaminate the patient. The scrubbing has to be complete and diligent and is not only time consuming, but in many cases, causes irritation to the skin. Further, since not all persons scrub in the same manner, the results achieved vary between persons and between scrubs by the same person. Also, while diligent scrubbing removes the surface bacteria, it has been found to have a lesser effect upon the bacteria present in the follicles and skin depressions. Obviously, any bacteria not removed may act as a contaminate to the patient during surgery. It has been shown that problems associated with pre-surgical scrubs include length of time involved, some bacteria not removed, difficulty in removing bacteria under and around fingernails, damage to tissue from repeated and long scrubbing operations, and sensitivity of the various individuals to certain disinfectants and detergents.

In an effort to overcome the disadvantages of the prior art method of pre-surgical scrubbing, U.S. Pat. No. 3,757,806 proposed a pulsating hydrojet lavage device which utilized pulsating jets of pressurized washing fluid for the purpose of quickly preparing personnel for cleanliness of the hands. The hands and arms of the individual to be scrubbed were inserted in a washing chamber comprising a curvilinear manifold arranged about longitudinal axis and subjecting the arms and hands to pulsating jets of a washing fluid discharged from the manifold device. The arm would be slowly rotated to achieve uniform exosure to the pulsating jets of washing fluid discharged from the manifold openings. It was found that when the lavage device was operated with a pulse frequency of approximately 1500 pulses per minute, the spray jets caused a compression-decompression effect on the human skin which was particularly effective in removing dirt and bacteria in the follicles and skin folds. Testing of the device showed that after both 50 PSI and 80 PSI lavage maintained for 90 seconds, the resulting cleanliness obtained was better than a conventional scrub of five minutes duration.

Although such device was found to be extremely effective in cleansing the skin in a very short time, it proved to be unsatisfactory in use for reasons other than the cleansing procedure and was discontinued. One of the disadvantages of the prior art lavage device was the extremely loud noise factor. The unit vibrated a great deal and was so loud in operation that it had to be placed in a particularly well isolated area in order to prevent the noise from bothering the patients and other individuals. This meant it could not be used in close proximity to operating rooms without somehow noise insulating the room in which the lavage device was located. One of the reasons for this noise was the use of tubing having square turns where the high pressure fluid would have to make a sudden change in direction. Further, the cleansing fluid pulsated. That is, it varied from 0 pressure to a maximum pressure some 1500 times per minute. Inasmuch as the fluid was pulsating, it struck the tubing at these right angle joints thus causing a great deal of slamming and vibration. Also, there was no way to really clean under and around the fingernails without curving the fingers and moving the hand back and forth under the various spray nozzles. In addition, the use of a pulsating jet, while being an effective cleanser of the skin, also proved to be irritating to the skin since the high pressure pulses had the effect of "slapping" the skin thus causing irritations after repeated use. Also, two people had to use the unit simultaneously with one individual having his arms and hands inside the lavage device while the other turned the operating switch "on" and after a predetermined time turned it "off". Further, the openings through which the hands and arms were inserted had no seals in order to prevent bacteria from transferring from an exterior source to the arms of the user when the arms were removed. Thus, the liquid splashed on the individual using the lavage device or else towels or other devices were wrapped about the arms to form ineffective seals and bacteria transferring sources.

SUMMARY

Thus, the present invention relates to a portable lavage device comprising a moveable tank for holding a cleansing liquid, pump means coupled to said tank for circulating said liquid under a varying pressure and spaced nozzle means coupled to said circulating pump and arranged to spray said liquid under said varying pressure against an item to be cleansed.

The novel invention also related to a method of cleansing an item comprising the steps of providing a cleansing fluid, circulating said fluid under pressure, varying said fluid pressure periodically from a maximum pressure to a minimum pressure and directing said fluid under said periodically varying pressure against said item to be cleansed.

BRIEF DESCRIPTION OF THE DRAWINGS

These and other objects of the instant invention may be had by referring to the following specification and drawings in which like numerals indicate like components and in which.

DESCRIPTION OF THE PREFERRED EMBODIMENT

Figure 1:
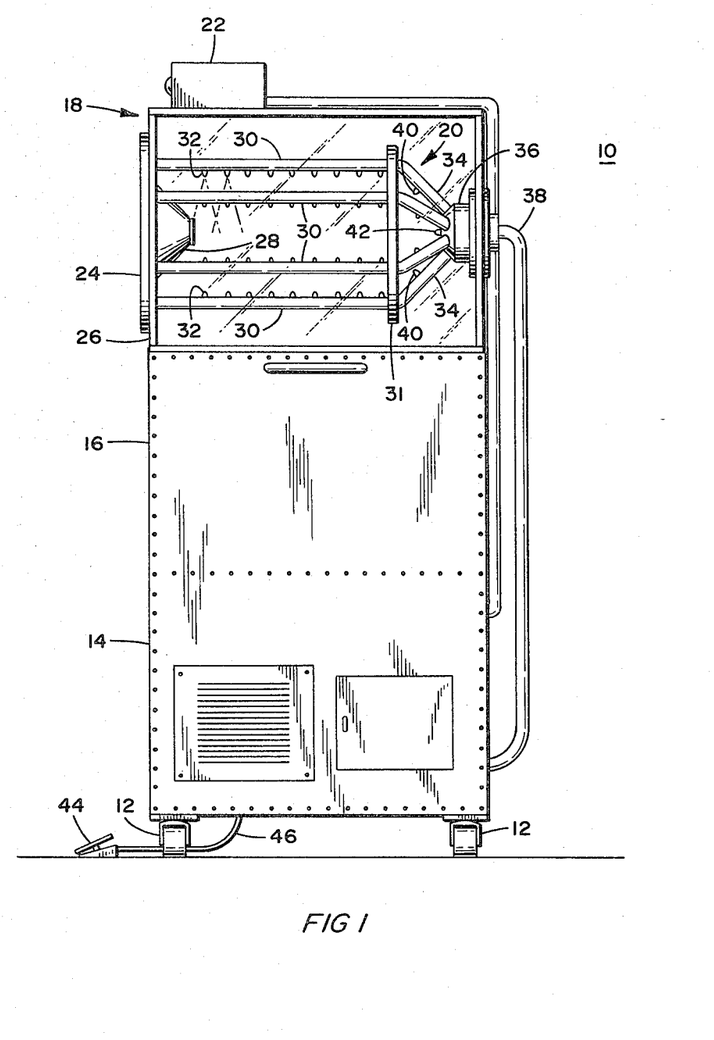
FIG. 1 is a side view of the novel, portable, lavage device.
Figure 2:
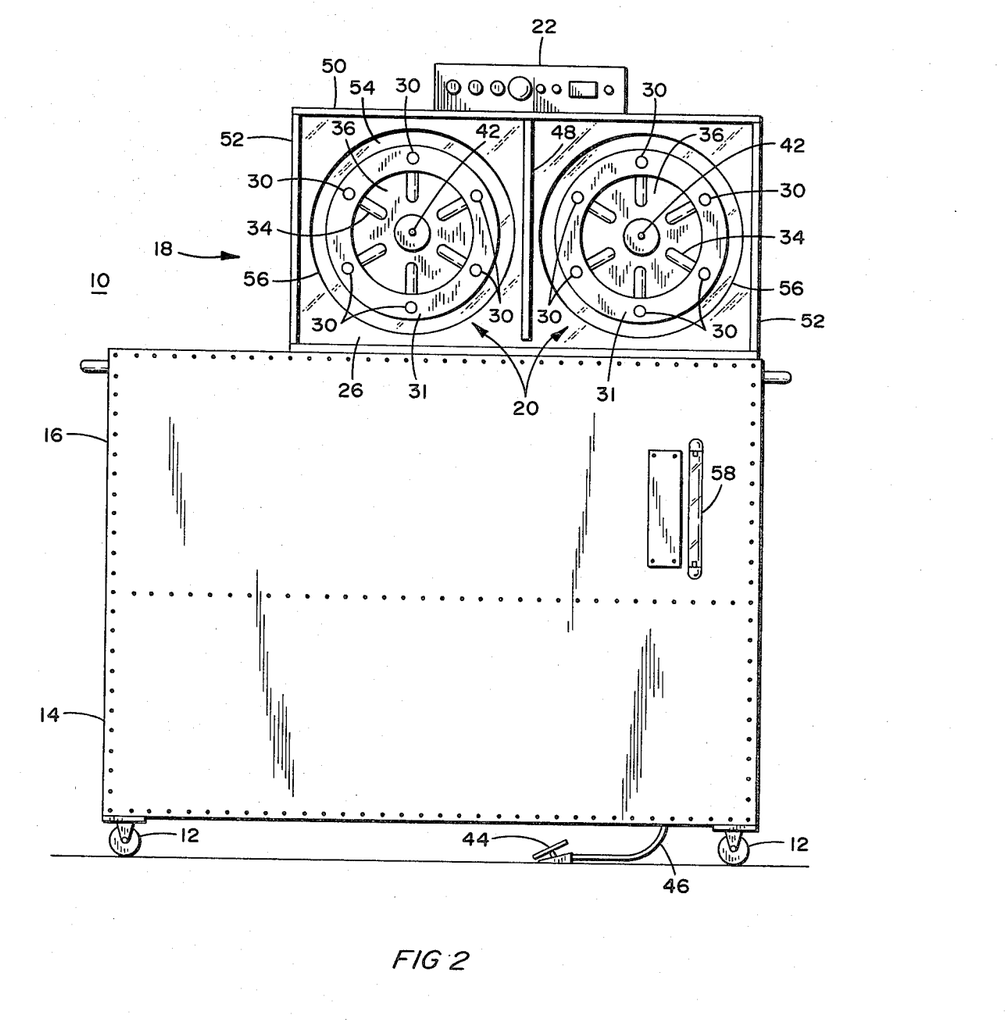
FIG. 2 is a front view of the device shown in FIG. 1.
Figure 3:
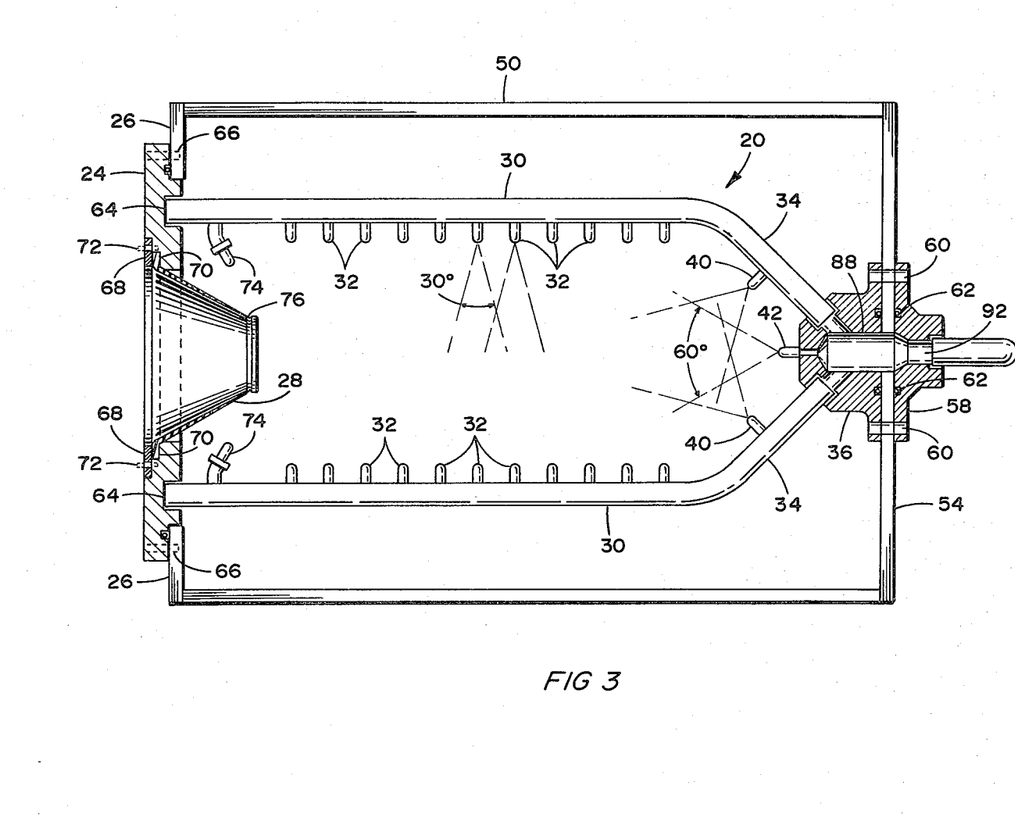
FIG. 3 is a side view, in partial cross-section, of one of the fluid distributing manifolds and its associated nozzles which direct the cleansing fluid against the item to be cleansed, for instance, arms and hands.
Figure 16:
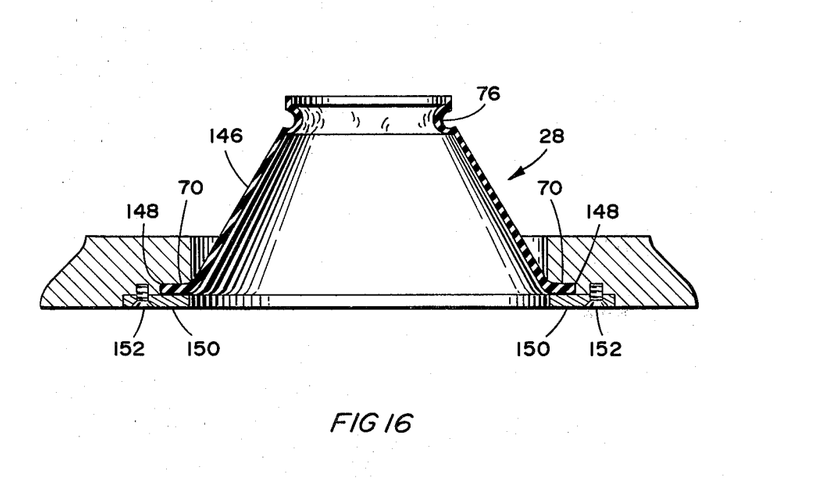
FIG. 16 is a cross-sectional view of the seal shown in FIG. 15.

FIG. 1 is a side view of the novel hydro scrubber 10 which is portable in nature and is therefore mounted on casters or wheels 12. The scrubber 10 has a mechanical portion 14 in which is located the pumps, valves, motors, and the like, a tank section 16 which contains the cleansing fluid and a manifold section 18 which includes the liquid dispensing manifold. An electronic control panel 22 sits on top of the unit and is used to turn on the electrical power, to electronically and automatically time the desired cleansing cycle and to select the frequency or number of times per minute the fluid is to be directed against the arms and hands being cleansed. Located in a mounting panel 24 and held in place by ring 26 shown in FIG. 3 and FIG. 16 is a rubber sleeve or boot 28 which is in the form of a truncated cone and through which the hand and arm may be inserted into the manifold section for cleansing. Manifold 20 includes a plurality of hollow tubes or pipes 30 each of which has a plurality of nozzles 32 (only a representative few of which are shown in FIG. 1 for clarity) directed inwardly toward the hand and arm of the user. The plurality of horizontal hollow tubes 30 are parallel to each other and are spaced in a circular pattern (as shown in FIG. 2) when viewed from either the front or back of said lavage device 10 and the plurality of spaced nozzles 32 spray liquid toward the hand and arm in the center of said circular pattern. Each of said tubes 30 has a portion 34 which is curved inwardly toward the center axis of said circular pattern where they attach to a circular manifold 36 which receives the cleansing fluid from a pipe 38 and distributes the fluid to the horizontal manifold tubes 30. Further, at least one spray nozzle 40 is located on the curved end portion 34 of the hollow tubes 30 and at least one spray nozzle 42 is mounted on the center of circular manifold 36 for spraying said liquid toward and perpendicular to the plane of said circular pattern for aiding in the cleansing of the fingernails of the user. A foot actuated switch 44 is attached to the lavage device 10 by means of electrical cable 46 whereby when each of the arms of the user are inserted into a corresponding rubber boot 28 for cleansing, the use of the foot on foot switch 44 can start the cleansing cycle.

FIG. 2 is a front view of the portable lavage device 10 shown in FIG. 1. Again, the unit is mounted on wheels 12 for portability and includes mechanical section 14, the fluid containing section 16, and the manifold section 18 which includes two liquid dispensing manifolds 20. It will be noted that there are two liquid dispensing manifolds so that one can be utilized for each arm and hand simultaneously. Also, foot actuated switch 44 is connected by cable 46 to the unit. The electronic control unit 22 sits on top of the device 10 and has the electrical power on/off switch, the timer meter and corresponding selector switch and the switch for controlling the frequency at which the cleansing fluid is directed against the skin of the user thereof. It will also be noted that a wall 48 separates the left and right liquid dispensing manifolds 20. Manifold section 18 is preferably made of a clear plastic including top wall 50, end walls 52, back wall 54, and the front wall 26 as shown in FIG. 1. The mounting panel 24 has been omitted in FIG. 2 within circle 56 in order to more clearly view the end of the parallel, horizontally spaced tubes 30 which form the liquid dispensing manifolds 20. A liquid level gauge 58 or any other device for indicating the level of the fluid within the storage tank 16 is shown on the front of said lavage device 10.

FIG. 3 is a side view of one of the fluid distributing manifolds 20 and its associated nozzles which direct the cleansing fluid against the items to be cleansed, for instance arms and hands. For purposes of clarity of FIG. 3, only two of the plurality of parallel, horizontally spaced tubes 30 are shown. Normally, six of tubes 30 are used as shown in FIG. 2. Again, it will be noted that each of said tubes 30 has a portion 34 of one end curved inwardly towards the center axis of the circular pattern formed by said horizontal hollow tubes 30 when viewed from the end of the tubes (as in FIG. 2) with each curved end 34 being mounted in an orifice on and supported by circular manifold 36. The circular manifold 36 is attached to the rear wall 54 by means of a manifold flange 58 with bolts or other fasteners which fit through orifices 60. Seal 62 forms a water tight connection with the back wall 54 and prevents any leakage from circular manifold 36 and manifold flange 58. The forward end of each of the horizontal hollow tubes 30 which form the manifold 20 are mounted in recesses 64 in mounting plate or panel 24. The mounting plate 24 is rigidly attached to front wall 26 by means of bolts, screws or other fasteners 66. Also attached to said mounting plate 26 is a rubber boot 28, shown in cross-section in FIG. 3, and which is held in place by a sealing ring 68 which mounts over the shoulders 70 of rubber boot 28 to hold it tightly in place. The sealing ring 68 may be fastened to the mounting plate 24 with screw 72 or other fastening means. As will be more clearly seen in relation to FIGS. 15 and 16 and described hereinafter, the rubber boot 28 allows the arm of the user to be inserted there-through into the cleansing chamber into the center of the circular pattern fromed by horizontal hollow tubes 30 each of which has a plurality of spaced nozzles 32 for spraying the cleansing liquid toward the center of said circular pattern.

It will be noted that the spray nozzles 40 on the curved end 34 of the spaced horizontal tubes 30 have a 60 degree spray angle as does nozzle 42 which is directly on the front end of circular manifold 36 while the nozzles 32 on the horizontal portion of spaced hollow tubes 30 have a 30 degree spray angle. The 60 degree angle on the spray nozzles 40 and 42 insure that the fingernails and fingers of the user of the lavage device are thoroughly encompassed and cleansed. It will also be noted that the spray nozzles 74 are positioned such that the end of the rubber boot 28 which is in contact with the arm of the user is continuously and completely sprayed with the cleansing fluid to insure that no germs can survive in that transition area between that part of the arm not to be cleansed and that part of the arm that is within the cleansing chamber of lavage device. It will be noted that rubber boot 28 has an indentation 76 formed in the truncated end of the conical shaped boot. This indentation 76 causes a secure fit about the arm of the user and, when the arm is withdrawn after the cleansing cycle is completed, the flexibility of rubber boot 28 and the snug fit of the indentation 76 about the arm of the user turns rubber boot 28 inside out as the arm is withdrawn thus keeping the sterilized interior side of the rubber boot 28 in contact with the sterilized arm thus preventing any germs or bacteria from making contact therewith as the arm is withdrawn.

Figure 4:
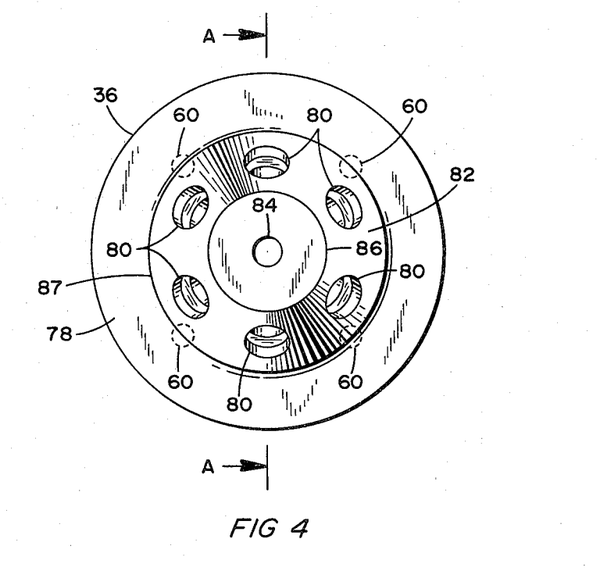
FIG. 4 is a front view of the manifold flange to which the manifold is connected and from which the manifold receives the cleansing fluid.

FIG. 4 is a front view of the circular flange 36 to which is attached the ends of the spaced, parallel, horizontal hollow tubes 30 forming the fluid distributing manifold 20. Orifices 60 are for the screws or bolts which attach the circular flange 36 to the rear wall 54 of the housing. These holes or orifices 60 are formed in flange 78 from which extends a cylindrical portion 87 having a slanted face 82 in which orifices 80 are formed and connect to the interior thereof and to the entrance port 88 shown in FIG. 3 and FIG. 5. On the flat front face 86 is an orifice 84 in which is mounted spray nozzle 42 as shown in FIG. 3.

Figure 5:
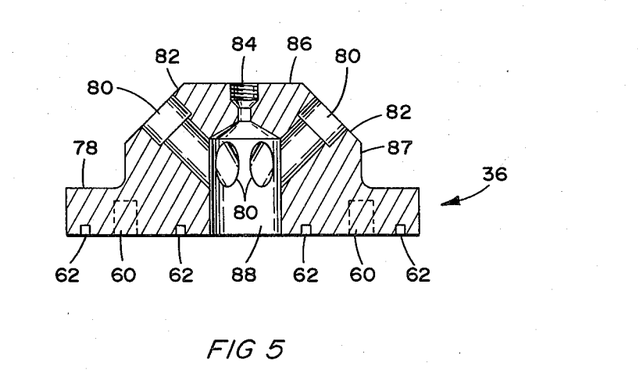
FIG. 5 is a cross-sectional view of the manifold flange of FIG. 4 taken along lines A—A.

FIG. 5 is a cross-sectional view of the circular flange 36 shown in FIG. 4 taken along lines A—A. As can be seen, the base has a flange 78 on the back side of which are orifices 60 which may have threads and extend partially into the base as shown in FIG. 5 or which may extend entirely through the base as shown in FIG. 3 but, in any case, which are used for attaching the circular flange 36 to the rear wall 54. Recesses 62 are used for seals to be placed therein to prevent fluid leakage between the circular flange 36 and the rear wall 54. The fluid enters inlet port 88 and exits through ports 80 to the horizontal hollow tubes 30 and through orifice 84 to nozzle 42. Again, it can be seen that cylindrical extension 87 which extends upwardly from base 78 has a face 82 forming a slanted edge thereof in which orifices 80 are located. The faces 82 are slanted at an angle sufficient to allow the curved ends 34 of the horizontal hollow tubes 30 to be mounted therein as shown in FIG. 3. Such an angle permits the cleansing fluid to enter the horizontal pipes 30 at a gentle angle instead of a right angle thus reducing the noise which would be generated if the fluid had to enter the orifices 80 and, thus tubes 30, at 90 degree angles.

Figure 6:
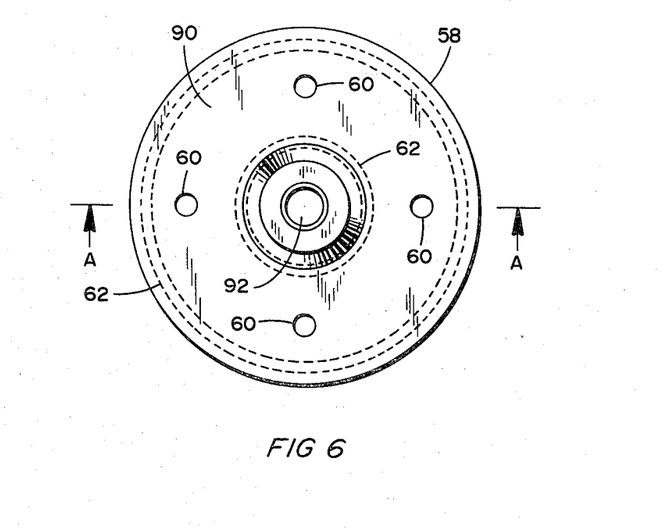
FIG. 6 is a front view of the intake flange which holds the manifold flange in FIG. 4 in place and provides a cleansing fluid to it.

FIG. 6 is a front view of the intake flange 58 which is shown in FIG. 3, and which cooperates with the circular flange 36 to carry the cleansing fluid from the pump to the distributing manifold 20. The flange simply is a flat plate 90 having orifices 60 therein through which screws or bolts or other fastening means are inserted to attach the intake flange to the circular flange as shown in FIG. 3.

Figure 7:
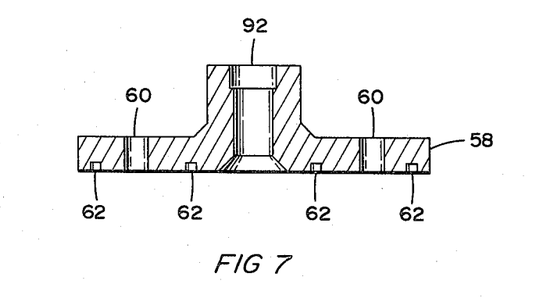
FIG. 7 is a cross-sectional view of the intake flange in FIG. 6 taken along lines A—A.

FIG. 7 is a cross-section view of the intake flange 58 taken along lines A—A of FIG. 6. Recesses 62 are for the purpose of placing seals therein to prevent any fluid leakage between the rear wall 54 and the intake flange 58. The fluid enters the flange through orifice 92 and communicates with the circular flange 78 as stated previously.

Figure 8:
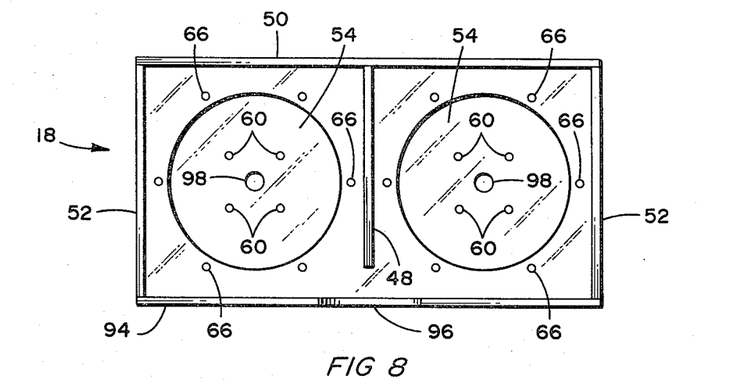
FIG. 8 is a front view of the housing assembly in which is located two fluid distributing manifolds separated by a wall thus allowing both arms and hands to be simultaneously cleansed.

FIG. 8 is a front view of the housing or manifold assembly 18 for containing the plurality of parallel, horizontally spaced tubes 30 as shown in FIG. 1. The housing assembly includes top wall 50, bottom wall 94, and side walls 52. Center wall 48 divides the housing into two chambers but, as shown, divider wall 48 only partially divides the two compartments. Bottom wall 94 is really the top wall of the fluid holding tank 16 and has therein an orifice 96 for draining the excess fluid back into tank 16 from either chamber formed by center divider wall 48 where the fluid can be recirculated. Back wall 54 has orifices 60 for bolts or screws or other attaching means to fasten the circular flange 36 and the intake flange 58 to the back wall 54. Orifice 98 communicates with the input orifice 88 of the circular flange 36 and receives fluid from orifice 92 on the intake flange 58. Orifices 66 in front wall 26 receives bolts, screws or other attaching means in order to fasten a front mounting plate 24 to the front wall 26 as shown in FIG. 3.

Figure 9:
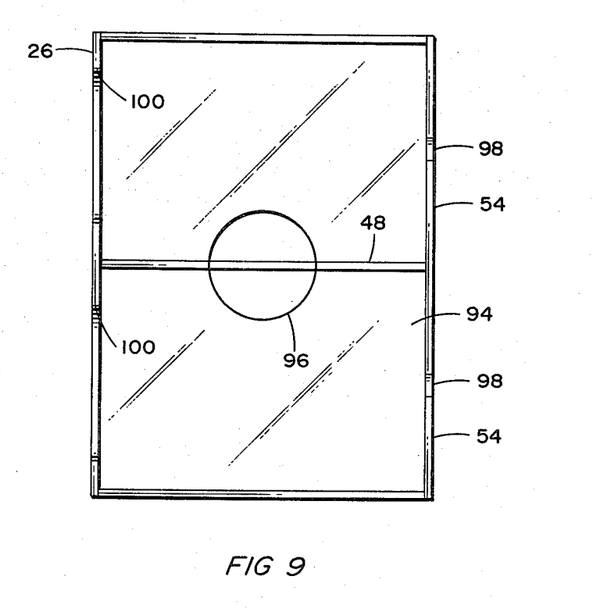
FIG. 9 is a top view of the housing assembly shown in FIG. 8.

FIG. 9 is a top view of the housing assembly shown in FIG. 8 and, in particular, illustrates the manner in which orifice 96 in bottom wall 94 extends partially into each of the chambers formed by divider wall 48 to drain the excess fluid therefrom. Further, orifice 98 is shown on back wall 54 for passing the cleansing fluid from the intake flange 58 to the circular flange 36. Also in front wall 26 is illustrated orifice 100 for receiving mounting plate 24. The preferred material for the top wall, side walls, back and front walls, and the bottom wall is one-half inch clear plexiglas although, of course, other materials such as any metal could be used so long as it resists corrosion.

Figure 10:
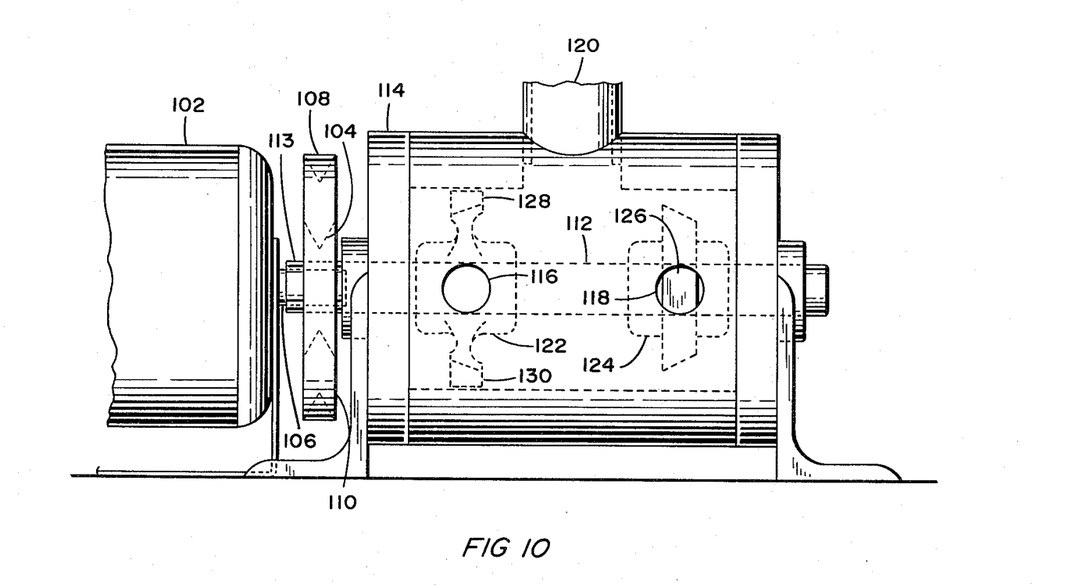
FIG. 10 is a front view of a housing and valves associated therewith which receives pressurized fluid and produces an output fluid to the fluid distributing manifolds which varies in pressure from a maximum pressure to a minimum pressure.

FIG. 10 is a front view of a housing and valves associated therewith which receive pressurized fluid and transmit a fluid to the fluid distributing manifolds which cyclically varies in pressure from a maximum pressure to a minimum pressure. One of the problems associated with the prior art is the fact that a pulsating jet of cleansing fluid is utilized. Because the cleansing fluid supply is turned alternately completely on and completely off at a high frequency, the sudden stopping and surging of the liquid creates a tremendous pounding which generates a noise level that is unacceptable. It is therefore necessary to vary the fluid pressure from a maximum to a minimum pressure cyclically without completely interrupting the flow of the cleansing fluid. Thus, in FIG. 10, a two speed motor 102 drives a V-belt pulley 104 through shaft 106. A V-belt 108 couples pulley 104 with a larger pulley 110 which is mounted on shaft 112. Shaft 112 extends into valve housing 114 which has two output ports 116 and 118 respectively and input port 120. The cleansing fluid enters input port 120 under pressure from a source such as a pump (not shown). Mounted on shaft 112 inside housing 114 are two impellers 122 and 124. As will be seen with respect to FIG. 12, impellers 122 and 124 are shaped generally in a figure eight configuration and are positioned 90 degrees apart. The width of the flanges forming the upper and lower portions of the figure eight design of the impellers is less than the diameter of the output ports 116 and 118 respectively. Thus, as can be seen in FIG. 10, flange 126 of impeller 124 is blocking orifice 118 to its maximum thus allowing only a small portion of the orifice 118 free to pass cleansing fluid to the fluid distrubuting manifold 20 to which it is connected. At the same time, however, impeller 122, which is 90 degrees rotationally spaced from impeller 124, has both its upper and lower flanges 128 and 130 clear of orifice 116 thus allowing maximum water pressure to pass to the fluid distributing manifold 20 to which this orifice is connected. Ninety degrees later, however, impeller 124 will have its flanges clear of orifice 118 while impeller 122 will have one of its upper or lower flanges 128 or 130 blocking orifice 116 to its maximum. Thus, the fluid being coupled to the fluid distributing manifold 20 from orifice 116 is at its maximum pressure. This unique construction allows the fluid to be distributed to each cleansing unit in each housing out of phase with each other thus allowing more quiet operation of the device.

Figure 11:
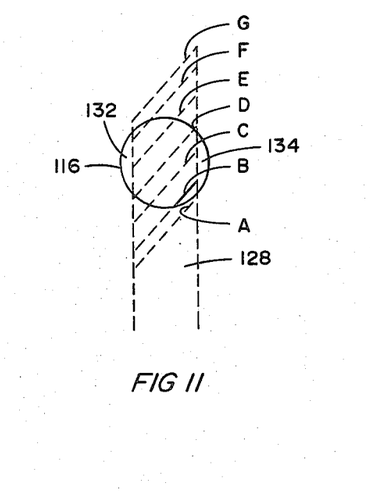
FIG. 11 is a view of one of the impellers as it passes an associated output port showing how the output port is decreased gradually in area to gradually and cyclically vary the pressure from a maximum when the output port is wide open to a minimum as the output port is gradually reduced in area to a minimum.

As stated earlier it is important that the fluid not be completely stopped, or pulsed, in order to reduce the noise level and to permit continued usage without irritation to the skin. This accomplished by the shape of the upper and lower flanges which form each of the impellers 122 and 124. As can be seen in FIG. 10, the flanges forming impellers 122 and 124 are beveled at an angle on each end thereof. Assume in FIG. 11 that flange 128 of impeller 122 is beginning to move into orifice 116. At point A, the flange is just outside the orifice and maximum pressure is being passed through the orifice 116. At point B, flange 128 has moved such that the tip of the flange is just entering orifice 116 and begins to gradually cut off the fluid flow. At point C, the tip of flange 128 has moved to a point whereby approximately one-fourth of the fluid flow has been reduced through orifice 116. At point D, the impeller 128 has moved sufficiently into orifice 116 to cut off approximately one-half of the fluid flow. At point E, the flange 128 of impeller 122 has moved sufficiently through orifice 116 to close off approximately three-fourths of the fluid flow and at point F, the flange 128 has moved sufficiently through orifice 116 to reduce the fluid flow almost to the minimum pressure. Finally, at point G, the flange 128 of impeller 122 has moved entirely into the orifice 116 thereby blocking fluid flow to the maximum such that fluid can pass only on each side 132 and 134 of flange 128.

Figure 12:
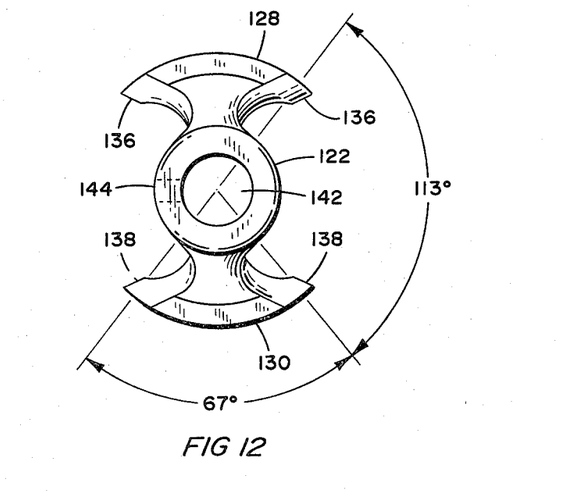
FIG. 12 is a front view of one of the impellers illustrated in FIG. 10 and FIG. 11.
Figure 13:
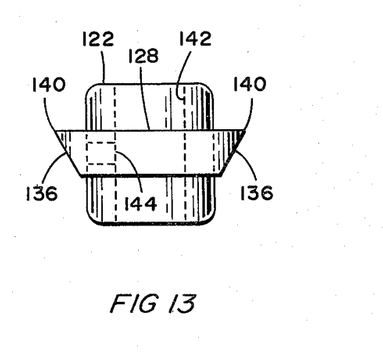
FIG. 13 is a top view of the impeller of FIG. 12.
Figure 14:
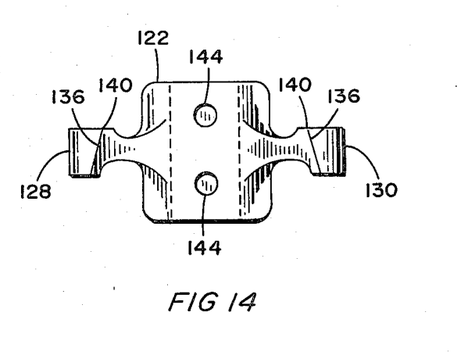
FIG. 14 is a side view of the impeller of FIG. 12.

Thus, it can be seen that the fluid pressure varies cyclically from a maximum pressure to a minimum pressure with a gradual change taking place between the point of the maximum pressure to the point of minimum pressure and vice-versa. This is extremely important because, as stated previously, a pulsating jet, wherein the fluid pressure is abruptly reduced to zero pressure and then abruptly increased to maximum pressure, creates a pounding and thus an unacceptable noise level. Further, with the motor 102 turning at 400 rpm, and with impellers 122 and 124 having a figure-eight configuration whereby each impeller flange passes its output orifice twice in one revolution, the resulting cleansing fluid is changed in pressure 800 times per minute and, if the motor speed is increased to 600 rpm, the pressure of the cleansing fluid is changed 1200 times per minute from a maximum to a minimum. This can be irritating on the skin when the water is pulsed or the pressure is changed from a zero pressure to maximum pressure. With the present invention where the pressure is changed from a maximum pressure to a minimum pressure in a gradual change and without a sharp burst, the skin is compressed and decompressed in order to be effective in removing dirt and bacteria in the follicles and skin folds and yet the irritating effects of a pulsed jet of fluid are not present. One of the impellers 122 is illustrated in FIG. 12, it being understood that the other impeller 124 is constructed in an identical manner. Impeller 122 has an upper flange 128 and a lower flange 130 and is generally in the shape of a figure-eight. Each end 136 of the upper flange 128 and each end 138 of the lower flange 130 is cut at an angle so as to form a point 140 as shown in FIG. 12. As explained previously, this enables one end of the impeller to enter its output orifice gradually to cut off the pressure and then the other end to leave the orifice gradually thus restoring the pressure and causing the cyclically varying pressure rather than a "pulsating" pressure. Orifice 142 is for the insertion of the drive shaft 112 which is coupled by the V-belts to motor 102. An orifice 144 allows a set screw or other type of fastening unit to attach the impeller 122 to shaft 112. Again, it is noted that the width of flange 128 is such that it does not completely block the output orifice 116 shown in FIG. 10. It has been found that the preferred ratio of the closed area of the output orifice to the area left open is 82% to 18%. This means that 82% of the output orifice 116 is closed when the impeller flange blocks the discharge opening to its maximum and 18% of the output orifice 116 is left open at that time. This allows approximately 117 gallons of fluid per minute to be transferred through the output orifice when the orifice is entirely opened and allows approximately 20 gallons per minute to flow in its semi-closed position. Thus the fluid pressure is cyclically varied from a maximum to a minimum pressure with a gradual change in between the two pressure limits. The minimum pressure that should be allowed is that which allows sufficiently quiet operation of the device as well as cleansing of the skin without irritation both of which objections occur when the fluid is pulsed or cut entirely off then suddenly turned on. It will also be noted that the length of the flanges 128 and 130 from approximately midway of one end 138 to midway of the other end 138 and midpoint of one end 136 to midpoint of the other end 136 is approximately 67 degrees while the corresponding open area between the two flanges 128 and 130 is approximately 113 degrees. This means that the output valve is open a greater length of time than it is closed thus causing a greater period of time when the arms and the hands are being cleansed with maximum pressure. FIG. 14 is a side view of the impeller 122.

Figure 15:
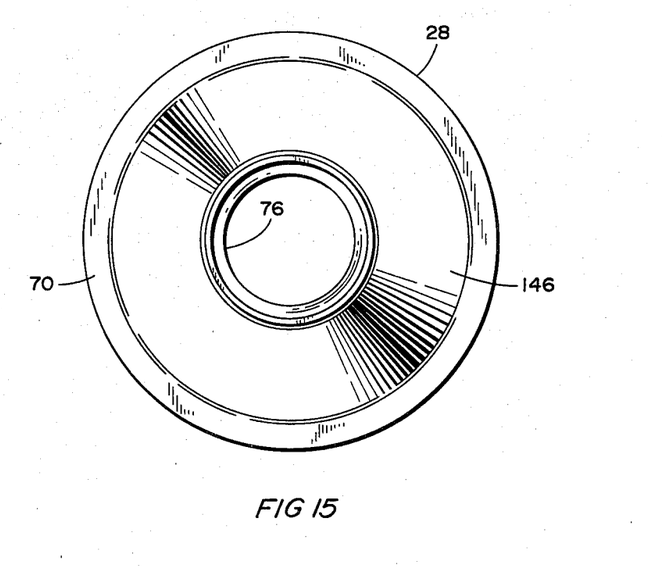
FIG. 15 is a front view of the rubber boot used as a seal with the novel lavage device.

FIG. 15 is a front view of the rubber boot 28 illustrated in FIG. 1 and includes a flange 70, a truncated cone body 146 and an indentation or groove 76 at the end thereof.

FIG. 16 illustrates how the rubber boot looks in cross-section when it is mounted in the mounting flange 24 shown in FIG. 1. The boot has a flange 70 which is placed in indentation 148 over which is placed a sealing ring 150 which is held in place by screws 152. Flange 70 is slightly thicker than indentation 148 but because it is made of rubber such as amtex latex rubber compound no. 15030, amber, it is held tightly in place. The rubber boot 28 has a truncated cone body 146 but terminates with a groove 76 at the end thereof through which the arm and hand must pass. This configuration is very important for hygenic purposes. When the arm is placed entirely inside the rubber boot to the interior of the lavage device, indentation 76 fits snugly about any size arm since it is made of rubber and therefore is elastic in nature. As can be seen in FIG. 3, nozzles 74 direct the cleansing fluid on the inside surfaces of the rubber boot 28 during the cleansing operation. When the arm is withdrawn, the indentation 76 holds firmly about the arm causing the rubber boot 28 to pull inside out as the arm is removed. When it is turned completely inside out and the arm is continued to be removed therefrom only the sanitized inside surface of the boot 28 comes in contact with the part of the body which has been cleansed. Thus the cleansed arm is not subjected to any part of the apparatus that has not been cleansed or that might contain germs. Thus, the indentation 76 illustrated in FIG. 16 keeps the arm in contact with the sterilized inner surface of rubber booth 28 while the arm and hand are being removed therefrom to prevent contamination of the cleansed arm and hand. Further, the U-shaped groove 76 allows different size arms to fit snugly in the rubber boot and still prevents blood cut off for the larger arm inasmuch as it is flexible and can give.

Also, as shown in FIG. 1, the electrical control unit 22 includes a timer built therein which can be set to any predetermined amount of time, for instance, 90 seconds, and which will also automatically shut the unit off when the preset amount of time has elapsed.

Thus, the present invention relates to a unique lavage device which saves valuable time with the possibility of saving human lives. It has a great number of advantages over a standard ten minute presurgical scrub including reducing the scrub time by as much as 85%, achieving consistent presurgical scrub results, causing much less irritation to the skin, providing cost and energy efficient use, increasing productivity with time saving, promoting enthusiasm for safety and cleanliness and removing more skin bacteria thus reducing risk of contamination.

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

What is claimed is:

1. A lavage device comprising:
   a. a tank for holding a cleansing fluid,
   b. pump means coupled to and operatively interconnected with said tank for circulating said cleansing fluid under a gradually varying pressure from a maximum to a minimum pressure to reduce noise during operation of the device and facilitate cleansing,
   c. spaced nozzle means coupled to and operatively interconnected with said circulating pump and arranged to discharge said fluid under said gradually varying pressure against an object to be cleansed, and
   d. said pump means including fluid flow restrictive means interconnecting with said nozzle means for gradually varying the pressure of said cleansing fluid during operation of said lavage device.

2. A device as in claim 1 wherein said spaced nozzle means comprises:
   a. a plurality of parallel, horizontal, hollow tubes spaced in a circular pattern when viewed from the end of said tubes and each of said tubes having a plurality of said spaced nozzles for spraying said cleansing liquid toward the center of said circular pattern, each of said tubes having a portion of one end curved inwardly toward the center axis of said circular pattern,
   b. a circular manifold having an inlet for receiving said fluid and a plurality of outlets extending outwardly and upwardly away from the center axis thereof, said manifold having a smaller diameter than said circular pattern of said hollow tubes, and
   c. means for connecting said manifold outlets to corresponding ones of said curved end portions of said spaced hollow tubes for delivering said cleansing fluid to said tubes.

3. A device as in claim 2 further including:
   a. a housing assembly for containing said plurality of parallel, spaced tubes, said housing including front, back, top, bottom and side walls, said circular manifold being mounted in said back wall,
   b. means for securing the front end of said hollow tubes to said front wall, and
   c. a rubber sleeve mounted in said securing means in the center of said hollow tube circular pattern, said sleeve providing an access to the interior of said housing assembly through which an arm and hand of a user may be inserted for cleansing.

4. A device as in claim 3 further including at least one spray nozzle on said curved end portion of each of said hollow tubes and at least one spray nozzle on the center of said circular manifold, said circular manifold nozzle spraying said liquid toward and perpendicular to the plane of said circular pattern for aiding in the cleansing of the fingernails of the user.

5. A device as in claim 4 wherein said sleeve comprises:
   a. a truncated cone of flexible material,
   b. a flange on the base of said cone for attaching said cone to said housing front wall,
   c. a cylindrical extension intergrally formed with and extending outwardly from the truncated end of said cone, and
   d. a groove formed along the periphery of said extension in a direction about the conical axis whereby variable diameter arms of users may be inserted through said cone into the interior of said housing, said groove forming a seal against said arms to prevent liquid escape and to cause said cone to turn inside out during removal of said arm thereby maintaining contact of the sterilized inside of said cone with the sterilized arm of the user.

6. A device as in claim 5 further including:
   a. a second housing assembly abutting the first housing assembly and containing a second set of parallel spaced hollow tubes coupled to a second manifold whereby both arms and hands may be cleansed simultaneously, and
   b. means for mounting said first and second housing assemblies on said tank, the top of said tank forming the bottom wall of said housing assembly and having an orifice therein whereby said used fluid may be collected and returned to said holding tank for recirculation.

7. A device as in claim 6 further including:
   a. a foot switch coupled to said pump means for energizing said pump with the foot while both arms are inserted through said sleeves into said housing assemblies, and
   b. a timer unit coupled to said pump means for allowing said pump to be energized for a predetermined period of time when said foot switch is actuated.

8. A device as in claim 7 wherein wheels are attached to said holding tank to make said device portable.

9. A device as in claim 8 further including means for selecting one of a plurality of frequencies of pressure variation of the fluid delivered by said pump.

10. A device as in claim 9 wherein said housing assemblies are made from clear plastic.

11. A portable lavage device comprising:
 a. a portable tank for storing a cleaning liquid and having a top cover with an orifice therein,
 b. first and second housing assemblies each having front, back, top and side walls and having a common wall extending from the top toward the bottom a partial distance, said housing assemblies being mounted on top of said portable tank,
 c. a hand and arm washing unit mounted in each of said housing assemblies,
 d. a fluid pump coupling the cleansing fluid in said tank to said washing units, said fluid pump circulating a cleansing fluid under varying pressure which cyclically varies from a maximum to a minimum,
 e. a foot operated switch coupled to said fluid pump for operating said pump,
 f. a timer coupled to said pump and said foot operated switch for enabling said pump to operate for a predetermined period of time, and
 g. a flexible seal mounted in the front wall of each of said housing assemblies through which the hands and the arms of the user may be inserted for cleansing.

12. A lavage device as in claim 11 wherein said washing unit comprises:
 a. a plurality of parallel, horizontal hollow tubes spaced in a circular pattern when viewed from the end of said tubes and each of said tubes having a plurality of spaced nozzles for spraying said liquid toward the center of said circular pattern, each of said tubes having a portion of one end curved inwardly toward the center axis of said circular pattern,
 b. a circular manifold mounted on the back wall of said housing assembly and having an inlet for receiving said fluid and a plurality of outlets extending outwardly and upwardly away from the center axis thereof, said manifold having a smaller diameter than said circular pattern of said hollow tubes, and
 c. means for connecting said manifold outlets to corresponding ones of said curved end portions of said spaced hollow tubes.

13. A lavage device comprising:
 a. a tank for holding a cleansing fluid,
 b. at least one cleansing unit interconnected with said tank for receiving an object to be cleansed,
 c. pump means operatively interconnected with and coupled to said tank and said cleansing unit for circulating said cleansing fluid under varying pressure to said cleansing unit for cleansing objects placed therein, said varying pressure gradually varying from a maximum to a minimum without pulsating to reduce noise during operation of the device and to facilitate cleansing of said objects, and
 d. said pump means including fluid flow restrictive means interconnected with said cleansing unit for gradually varying the pressure of said cleansing fluid during operation of said lavage device.

14. A lavage device as in claim 13 wherein said washing unit comprises:
 a. a housing assembly having a top, back and side walls and a bottom wall formed by said tank,
 b. a cleaning unit comprising a plurality of parallel, horizontal, hollow tubes mounted in said housing assembly and spaced in a circular pattern when viewed from the end of said tubes, each of said tubes having a portion of one end thereof curved inwardly toward the center axis of said circular pattern,
 c. a circular manifold having an inlet for receiving fluid from said tank and a plurality of outlets extending upwardly and outwardly from the center axis thereof, said circular manifold being mounted in said housing back wall and having a smaller diameter than said circular pattern of said hollow tubes,
 d. means connecting said manifold outlets to corresponding ones of said curved end portions of said spaced hollow tubes, and
 e. a plurality of spaced nozzles on each of said hollow tubes for spraying said liquid toward the center of said circular pattern.

15. A lavage device as in claims 1 or 11 further including:
 a. valve means coupled between said circulating pump and said nozzle means for causing said liquid pressure to cyclically vary between a maximum and minimum pressure.

16. A lavage device as in claim 15 wherein said valve means comprises:
 a. a housing having an input port and an output port,
 b. at least one impeller within said housing for alternately opening and partially closing said output port to cause said cyclical variation in said fluid pressure.

17. A device as in claim 16 wherein said output port is smaller in area than said input port.

18. A device as in claim 17 further including:
 a. two output ports,
 b. two cleansing units, each one connected to an output port; and
 c. an impeller for each output port for alternately opening and partially closing its associated one of said output ports whereby fluid with a cyclically varying pressure is coupled to each of said cleansing units.

19. A device as in claim 18 wherein:
 a. said impellers are mounted on and driven by a common shaft, and
 b. said impellers are rotated 90 degrees with respect to each other whereby the output ports alternately open and partially close thereby delivering said fluid to said cleansing units out of phase with each other.

20. A device as in claim 19 wherein each impeller is shaped generally as a figure-eight thereby opening and partially closing its associated output port twice for each revolution of the impeller.

21. A lavage device comprising:
 a. a tank for storing a cleansing fluid and having an opening through said fluid may be placed in said tank,
 b. first and second housing assemblies having a common wall extending in a direction from the top toward the bottom a partial distance, said housing assemblies being mounted on said tank,
 c. a hand and arm washing unit mounted in each of said housing assemblies, d. a fluid pump coupling the cleansing fluid in said tank to said washing units, said fluid pump circulating said cleansing fluid under varying pressure which gradually varies from a maximum to a minimum, e. an actuating switch coupled to said fluid pump for operating said pump, and f. a flexible seal mounted in a vertical wall of each of said housing assemblies through which the hands and arms of the user may be inserted for cleansing.

* * * * *